(12) United States Patent
Marquis et al.

(10) Patent No.: US 6,503,891 B1
(45) Date of Patent: Jan. 7, 2003

(54) WATER EMULSIFIABLE FORMULATIONS

(75) Inventors: Edward T. Marquis; George P. Speranza; Howard P. Klein, all of Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/652,437

(22) Filed: Aug. 31, 2000

(51) Int. Cl.[7] .................. A01N 57/00; A01N 43/00; A01N 43/54; A61K 31/67; A61K 31/505

(52) U.S. Cl. .................. 514/95; 514/183; 514/269

(58) Field of Search .................. 514/95, 269, 183; 424/405

(56) References Cited

U.S. PATENT DOCUMENTS

| | | | |
|---|---|---|---|
| 3,899,578 A | 8/1975 | Bird et al. ............... | 424/81 |
| 5,531,995 A | 7/1996 | Lubetzky et al. ......... | 424/409 |
| 5,731,264 A | 3/1998 | Narayanan et al. ....... | 504/116 |
| 5,931,994 A | * 8/1999 | Herrero ................ | 106/15.05 |

FOREIGN PATENT DOCUMENTS

| | | |
|---|---|---|
| CZ | 112134535 | 1/1989 |
| DE | 19613334 | * 10/1997 |
| EP | 0189588 | 12/1985 |
| FR | 2138929 | 5/1972 |
| JP | 9002904 | 1/1997 |
| JP | 2000143409 | * 5/2000 |
| WO | WO 99/39581 | 8/1999 |

OTHER PUBLICATIONS

Ganeshkumar et al, Studies on the efficacy of some chemical combinations in controlling the powdery mildew disease on bhendi*

* cited by examiner

*Primary Examiner*—Alton N Pryor
(74) *Attorney, Agent, or Firm*—O'Keefe, Egan & Peterman LLP

(57) ABSTRACT

A composition comprising an organic carbonate such as propylene carbonate and O,O-diethyl-O-(2-isopropyl-4-methyl-6-pyrimidinyl)phosphorothioate, S-[1,2-bis(ethoxycarbonyl)ethyl]O,O-dimethylphosphorodithioate, or 6,7,8,9,10, 10-hexachloro-1,5,5a,6,9,9a-hexahydro-6,9-methano-2,4,3-benzodioxathiepin-3-oxide, and methods thereof.

25 Claims, No Drawings

WATER EMULSIFIABLE FORMULATIONS

BACKGROUND OF INVENTION

This invention relates to stable, water-emulsifiable compositions of O,O-diethyl-O-(2-isopropyl-4-methyl-6-pyrimidinyl)phosphorothioate (DIAZINON insecticide), S-[1,2-bis(ethoxycarbonyl)ethyl]O,O-dimethylphosphorodithioate (MALATHION insecticide), or endosulfan and an organic carbonate solvent. More particularly, this invention relates to compositions containing, as the organic carbonate, alkylene carbonate or dialkyl carbonate or both.

Xylene, kerosene, and cyclohexanone have been used as solvents in agricultural formulations containing O,O-diethyl-O-(2-isopropyl-4-methyl-6-pyrimidinyl)phosphorothioate, S-[1,2-bis(ethoxycarbonyl)ethyl]O,O-dimethylphosphorodithioate, or endosulfan. These solvents, however, are believed to be toxic to humans, high volatility, high flash point, and/or poor biodegradability. Due to the deficiencies and disadvantages of conventional compositions that contain these solvents in combination with O,O-diethyl-O-(2-isopropyl-4-methyl-6-pyrimidinyl)phosphorothioate, S-[1,2-bis(ethoxycarbonyl)ethyl]O,O-dimethylphosphorodithioate, or endosulfan, new compositions are highly desirable.

SUMMARY OF INVENTION

The invention provides a solution to one or more of the problems and disadvantages discussed above.

In one broad respect, this invention is a composition comprising an organic carbonate and O,O-diethyl-O-(2-isopropyl-4-methyl-6-pyrimidinyl)phosphorothioate, S-[1,2-bis(ethoxycarbonyl)ethyl]O,O-dimethylphosphorodithioate, or 6,7,8,9,10, 10-hexachloro-1,5,5a,6,9,9a-hexahydro-6,9-methano-2,4,3 - benzodioxathiepin-3-oxide. The organic carbonate and the O,O-diethyl-O-(2-isopropyl-4-methyl-6-pyrimidinyl)phosphorothioate, S-[1,2-bis(ethoxycarbonyl)ethyl]O,O-dimethylphosphorodithioate, or 6,7,8,9,10, 10-hexachloro-1,5,5a,6,9,9a-hexahydro-6,9-methano-2,4,3-benzodioxathiepin-3-oxide may be present in amounts effective to form a water emulsifiable composition. Generally, the amount of the organic carbonate in the composition may vary from about 5 percent by weight to about 95 percent by weight, based on the total weight of the composition. Generally, the amount of O,O-diethyl-O-(2-isopropyl-4-methyl-6-pyrimidinyl)phosphorothioate, S-[1,2-bis(ethoxycarbonyl)ethyl]O,O-dimethylphosphorodithioate, or 6,7,8,9,10, 10-hexachloro-1,5,5a,6,9,9a-hexahydro-6,9-methano-2,4,3-benzodioxathiepin-3-oxide may vary from about 95 percent by weight to about 5 percent by weight, based on the total weight of the composition. 0,0-diethyl-0-(2-isopropyl-4-methyl-6-pyrimidinyl)phosphorothioate is available commercially under the name DIAZINON. S-[1,2-bis(ethoxycarbonyl)ethyl]O, O-dimethylphosphorodithioate is available commercially under the name MALATHION. 6,7,8,9,10,1 0-hexachloro- 1,5,5a,6,9,9a-hexahydro-6,9-methano-2,4,3-benzodioxathiepin-3-oxide is also known as endosulfan. The composition may also include a co-solvent, a surfactant, an emulsifier, or combination thereof.

In another broad respect, this invention is a process for forming a composition of O,O-diethyl-O-(2-isopropyl-4-methyl-6-pyrimidinyl)phosphorothioate, S-[1,2-bis(ethoxycarbonyl)ethyl]O,O-dimethylphosphorodithioate, or endosulfan, comprising: combining the O,O-diethyl-O-(2-isopropyl-4-methyl-6-pyrimidinyl)phosphorothioate, S-[1,2-bis(ethoxycarbonyl)ethyl]O,O-dimethylphosphoroditioate, or endosulfan with an organic carbonate. In one aspect, this process may also include the addition of water to form an emulsion. The emulsion may then be sprayed by the end user, such as being sprayed on crops.

In another broad respect, this invention is a method of supplying an organic carbonate for use in insecticide compositions, comprising: providing the organic carbonate for a permitted use in formulations comprising an insecticide and an organic carbonate. If necessary, decisions may be appealed to the courts in the United States. The formulations are as described herein and may include other insecticides, herbicides, pesticides, and other agriculturally active compounds apart from diazinon, malathion, and endosulfan, and may include other cosolvents and/or other components.

This composition may be used by applying it to an area to be treated for a given insect. The amount of insecticide may vary in accordance with known principles. O,O-diethyl-O-(2-isopropyl4-methyl-6-pyrimidinyl)phosphorothioate, S-[1,2-bis(ethoxycarbonyl)ethyl]O,O-dimethylphosphorodithioate, and endosulfan are known insecticides. The application is generally performed by mixing the composition with water to form an emulsion. This invention in another broad respect is a process useful for applying an insecticide composition, comprising: mixing water and an insecticide composition to form an emulsion, and applying the emulsion on a surface, wherein the insecticide composition comprises an organic carbonate and O,O-diethyl-O-(2-isopropyl-4-methyl-6-pyrimidinyl)phosphorothioate, S-[1,2-bis(ethoxycarbonyl)ethyl]O, O-dimethylphosphorodithioate, or 6,7,8,9,10,10-hexachloro- 1,5,5a,6,9 ,9a-hexahydro-6,9-methano-2,4,3-benzodioxathiepin-3-oxide. The emulsion may be applied in a variety of well known ways, such as by spraying. The surfaces to be treated may vary widely, such as on the ground, dirt, rock, lumber, plants, lawns, trees, in and around buildings, and other surfaces that are treated with these insecticides conventionally.

This invention has a number of advantages. For example, the compositions have several important attributes, including low toxicity, high flash point, good biodegradability of the transport system (the organic carbonate, other solvent(s), and any surfactant). It has further been advantageously found that the compositions may be blended with additional co-solvents, activators, and the like, or may be used directly. Furthermore, in the case of propylene carbonate, the propylene carbonate breaks down into propylene glycol, which is non-toxic. Hence, the propylene carbonate compositions of this invention are environmentally friendly, particularly as compared to aromatic hydrocarbons previously used to form compositions with the In another broad respect, this invention is a process for forming a concentrated composition of O,O-diethyl-O-(2isopropyl4-methyl-6-pyrimidinyl)phosphorothioate, S-[1,2-bis(ethoxycarbonyl)ethyl]O, dimethylphosphorodithioate, or endosulfan. The compositions of this invention may advantageously be of low volatility and free of carcinogenic chemicals. Advantageously, the compositions may be formulated into water emulsifiable concentrates. Likewise, the compositions may be formulated to contain the same amount of active ingredient (O,O-diethyl-O-(2-isopropyl4-methyl-6-pyrimidinyl)phosphorothioate, S-[1,2-bis(ethoxycarbonyl)ethyl]O,O-dimethylphosphorodithioate, or endosulfan) per gallon as in presently registered commercial formulations. Advantageously, when diluted with water, the formulations of the present invention may have less than 1 percent solids fallout after 1 hour when subjected to an accelerated stability test at 50 degrees Centigrade.

DETAILED DESCRIPTION OF THE INVENTION

The compositions of this invention contain a carbonate such as alkylene carbonate or dialkyl carbonate or both.

The organic carbonates that may be employed in the practice of this invention include alkylene carbonates (cyclic compounds) and dialkyl carbonates. In general, the organic carbonates contain a low number of carbon atoms. The alkylene carbonate used in the present invention can contain from 2 to 10 carbon atoms. Representative examples of alkylene carbonates that may be employed in the practice of this invention include ethylene carbonate and propylene carbonate. Mixtures of carbonates may also be employed. In the practice of this invention, alkylene carbonates are preferred, and among the alkylene carbonates propylene carbonate is preferred. The dialkyl carbonate used in the present invention may contain from 3 to 25 carbon atoms. The dialkyl carbonate may be of formula R—$CO_3$—R', wherein R and R' may be the same or different, and may independently in each occurrence be alkyl of from 1 to about 12 carbon atoms. In one embodiment, the dialkyl carbonate may be dimethyl carbonate, diethyl carbonate, or a mixture thereof. The amount of alkylene carbonate, dialkyl carbonate or both used in the practice of this invention may vary widely. Typically the total amount of carbonate is from about 0.1 to about 97 percent by weight of the total composition. In one embodiment, the amount is from about 5 to about 95 percent by weight. In another embodiment, the amount is from about 10 to about 90 percent by weight.

For the compositions that contain O,O-diethyl-O-(2-isopropyl-4-methyl-6-pyrimidinyl)phosphorothioate, the organic carbonate serves to dissolve the O,O-diethyl-O-(2-isopropyl-4-methyl-6-pyrimidinyl)phosphorothioate. A surfactant may be added so that when the formulation is mixed with water, an emulsion may be formed.

In addition to the components described above, it is contemplated that the compositions of this invention may optionally contain activators such as formic or oxalic acid, thickeners, surfactants, acids or bases, stabilizers, corrosion inhibitors, and other additives commonly used in paint removers.

Non-limiting examples of representative surfactants which may optionally be used in the practice of this invention include non-ionic, anionic, cationic and amphoteric surfactants, such as monocarboxyl cocoimidoazoline, higher alkyl sulfate sodium salts, tridecyloxy poly(alkyleneoxy ethanol), ethoxylated or propoxylated alkyl phenol, alkyl sulfoamides, C10–18 alkaryl sulfonates such as alkylbenzene sulfonates, cocoamphaodipropionate, cetylpalmitic alkanol amides, hydrogenated castor oil, isooctylphenyl polyethoxy ethanol, sorbitan monopalmitate, C8–18 alkyl pyrrolidone, cocoaminoprpionic acid and polyethoxy amino salts thereof. When used, the amount of surfactant should be sufficient to render the composition miscible. If used, the amount of surfactant is typically from about 0.1 to about 10 percent by weight of the total composition.

The compositions of this invention may also optionally contain a wide variety of other organic cosolvents. Likewise, the present invention may be practiced in the absence of one or more of such solvents. Non-limiting examples of representative classes of such other cosolvents include hydrocarbons, ethers, phenols, glycols, lactones, chlorinated hydrocarbons, aromatic hydrocarbons nitrated hydrocarbons, dibasic esters, mono-esters such as ethyl acetate, butyl acetate, ethyl-3-ethoxy-propionate, propylene glycol methyl ether acetate, propylene glycol butyl ether acetate, dipropylene glycol methyl ether acetate, dipropylene glycol butyl ether acetate and cyclic esters such as butyrolactone, organic sulfur-containing compounds dimethylsulfoxide (DMSO) and sulfolane, ketones that may be used in the practice of this invention include acetone, methyl ethyl ketone (MEK), 5-methyl-2-hexanone (MIAK), methyl isobutyl ketone and methyl isoamylbutone, glycol ethers such as propylene glycol methyl ether (PM), dipropylene glycol methyl ether (DPM), or dipropylene glycol n-butyl ether (DPNB), ethylene glycol butyl ether (EB) and dipropylene glycol butyl ether (DB), alcohols such as methanol, ethanol, propanol, butanol, benzyl alcohol, and amides. Such cosolvents may be polar or non-polar, may be protic or aprotic, may be cyclic, branched, or straight-chain, and may contain one or more functional groups. Representative examples of common hydrocarbon solvents include hexane, toluene, xylene, and mixtures of aliphatic and aromatic hydrocarbons. Representative examples of common ether solvents include dibutyl ether, ethyl ether, and diphenyl ether. Representative examples of common phenols include phenol and the cresols and resorinols. Representative examples of common glycol solvents include ethylene, propylene and butylene glycols as well as methyl propane diol. Representative examples of common chlorinated hydrocarbon solvents include methylene chloride, methyl chloroform, chlorobenzenes and dichlorobenzenes. Representative examples of common nitrated hydrocarbon solvents include nitroethane and nitropropane. Representative examples of common amide solvents include formamide, dimethyl formamide, acetamide, and dimethylacetamide.

When a given composition containing a given carbonate does not form a miscible composition, a co-solvent may be used to provide a miscible composition. For instance, a glycol ether may be added as a co-solvent in an amount effective to solubilize the components of the mixture. Such glycol ethers may be included for other purposes as well. Such amounts may vary depending on the specific composition of interest, as one of skill in the art may appreciate. The particular type and amount of glycol ether which will afford a miscible composition may be identified by routine experimentation. Also, an alcohol or alkylene carbonate may be beneficially employed as a co-solvent to provide miscible dialkyl carbonate compositions of this invention.

The conditions under which the components are mixture to form the compositions of this invention may vary considerably. In general, the mixing may be achieved on large scales by use of mechanized stirrers. The components may be added individually or concurrently. This may be done at a variety of temperatures including from about 0 to about 100 degrees Centigrade.

The following examples are illustrative of this invention and are not intended to be limit the scope of the invention or claims hereto. Unless otherwise denoted all percentages are by weight.

EXAMPLE-DIAZINON FORMULATION

A O,O-diethyl-O-(2-isopropyl-4-methyl-6-pyrimidinyl) phosphorothioate formulation was prepared and mixed according to the following formula:

|  | Lbs/U.S. gallon | Percent by weight |
| --- | --- | --- |
| Diazinon (technical grade, 93%) | 4.35 | 45.27 |
| ALKASURF OP-10[a] | 0.55 | 5.73 |
| Propylene carbonate | 4.70 | 49.00 |
|  | 9.60 | 100.00 |

[a]A surfactant of an octyl phenol with 10 moles of ethylene oxide added to the phenol group, and supplied by Rhodia, Inc.

This formulation had a specific gravity at 20 degrees Centigrade of 1.1530. The composition was homogenous. The formulation was then diluted with three different hardness water (1:100 formulation:water dilution) to form three emulsion samples which were subjected to an accelerated stability testing where two weeks at 50 degrees Centigrade approximates one year at ambient temperature with the following results:

EXAMPLE-MALATHION FORMULATION

A S-[1,2-bis(ethoxycarbonyl)ethyl]O,O-dimethylphosphorodithioate formulation was prepared and mixed according to the following formula:

|  | Lbs/U.S. gallon | Percent by weight |
| --- | --- | --- |
| Malathion (technical grade, 92%) | 5.48 | 54.60 |
| TOXIMUL MP-26[b] | 0.79 | 7.88 |
| Propylene carbonate | 3.77 | 37.52 |
|  | 10.04 | 100.00 |

[b]A blend of nonionic surfactant and a dodecyl benzene sulfonate (DDBS).

This formulation had a specific gravity at 20 degrees Centigrade of 1.206. The composition was homogenous. The formulation was then diluted with three different hardness water (1:100 formulation:water dilution) to form three emulsion samples which were subjected to an accelerated stability testing where two weeks at 50 degrees Centigrade approximates one year at ambient temperature with the following results:

| Water Hardness | Dispersion | Cream | Percent fallout over time | | | | | | |
| --- | --- | --- | --- | --- | --- | --- | --- | --- | --- |
| | | | Initial | | | | Reagitation | | |
| | | | 10 min | 30 min | 60 min | 24 hrs | 10 min | 30 min | 60 min |
| 150 | Good | Small | 0.25 | 0.40 | 0.50 | 0.70 | 0.25 | 0.40 | 0.50 |
| 500 | Good | Small | 0.35 | 0.50 | 0.55 | 0.65 | 0.3 | 0.45 | 0.55 |
| 800 | Good | Small | 0.25 | 0.35 | 0.45 | 0.60 | 0.20 | 0.40 | 0.50 |

It was seen based on this data that the formulation has good dispersion, very small or acceptable cream, and an acceptably small percent of solids fallout over time.

| Water Hardness | Dispersion | Cream | Percent fallout over time | | | | | | |
| --- | --- | --- | --- | --- | --- | --- | --- | --- | --- |
| | | | Initial | | | | Reagitation | | |
| | | | 10 min | 30 min | 60 min | 24 hrs | 10 min | 30 min | 60 min |
| 150 | Good | Small | nil | nil | nil | 0.60 | nil | nil | nil |
| 500 | Good | Small | nil | nil | nil | 0.80 | nil | nil | nil |
| 800 | Good | Small | nil | nil | nil | 0.80 | nil | nil | nil |

It was seen based on this data that the formulation has good dispersion, very small or acceptable cream, and an acceptably small percent of solids fallout over time.

EXAMPLE - ENDOSULFAN FORMULATION

A endosulfan formulation was prepared and mixed according to the following formula:

|  | Lbs/U.S. gallon | Percent by weight |
|---|---|---|
| Endosulfan (technical grade, 95%) | 2.12 | 21.65 |
| MAKON 6[c] | 0.58 | 5.92 |
| MAKON 10[d] | 0.40 | 4.08 |
| EPOXOL 7-4[e] | 0.10 | 1.02 |
| Propylene carbonate | 4.51 | 46.08 |
|  | 9.79 | 100.00 |

[c] A nonyl phenol ethoxylate wherein six ethylene oxides were added to the phenol groups.
[d] A nonyl phenol ethoxylate wherein ten ethylene oxides were added to the phenol groups.
[e] An epoxidized soybean oil, supplied by Guelph Soap Co., Inc.

This formulation had a specific gravity at 20 degrees Centigrade of 1.1750. The composition was homogenous. The formulation was then diluted with three different hardness water (1:100 formulation:water dilution) to form three emulsion samples which were subjected to an accelerated stability testing where two weeks at 50 degrees Centigrade approximates one year at ambient temperature with the following results:

| Water Hardness | Dispersion | Cream | Percent fallout over time | | | | | | |
|---|---|---|---|---|---|---|---|---|---|
|  |  |  | Initial | | | | Reagitation | | |
|  |  |  | 10 min | 30 min | 60 min | 24 hrs | 10 min | 30 min | 60 min |
| 150 | Good | Very Small | 0.30 | 0.40 | 0.50 | 0.75 | 0.35 | 0.50 | 0.55 |
| 500 | Good | Very Small | 0.30 | 0.40 | 0.50 | 0.75 | 0.30 | 0.50 | 0.60 |
| 800 | Good | Very Small | 0.20 | 0.30 | 0.35 | 0.50 | 0.20 | 0.30 | 0.35 |

It was seen based on this data that the formulation has good dispersion, very small or acceptable cream, and an acceptably small percent of solids fallout over time.

As used in herein and the claims, the word "a" is not intended to imply one and only one element is required; rather, as used herein and in the claims "a" means one or more.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A composition consisting essentially of an organic carbonate; O,O-diethyl-O-(2isopropyl-4-methyl-6-pyrimidinyl)phosphorothioate, or S-[1,2-bis(ethoxycarbonyl)ethyl]O, O-dimethylphosphorodithioate; optionally a co-solvent; and optionally a surfactant; wherein the carbonate is an alkylene carbonate containing from 2 to 10 carbon atoms.

2. The composition of claim 1, wherein the carbonate is propylene carbonate or ethylene carbonate or both.

3. The composition of claim 1, wherein the carbonate is ethylene carbonate or propylene carbonate.

4. The composition of claim 1, wherein the co-solvent is present.

5. The composition of claim 1, wherein the surfactant is present.

6. The composition of claim 1, wherein the organic carbonate is present in an amount from 10 to about 90 percent by weight of the composition.

7. A process for forming a composition of O,O-diethyl-O-(2-isopropyl4-methyl-6-pyrimidinyl)phosphorothioate, or S-[1,2-bis(ethoxycarbonyl)ethyl]O, O-dimethylphosphorodithioate, or endosulfan, consisting essentially of: combining the O,O-diethyl-O-(2-isopropyl-4-methyl-6-pyrimidinyl)phosphorothioate, or S-[1,2-bis(ethoxycarbonyl)ethyl]O,O-dimethylphosphorodithioate, with an organic carbonate, optionally a co-solvent, and optionally a surfactant; wherein the carbonate is an alkylene carbonate containing from 2 to 10 carbon atoms.

8. The process of claim 7, wherein the carbonate is an alkylene carbonate containing from 2 to 10 carbon atoms.

9. The process of claim 7, wherein the carbonate is propylene carbonate or ethylene carbonate or both.

10. The process of claim 7, wherein the carbonate is ethylene carbonate or propylene carbonate.

11. The process of claim 7, wherein the co-solvent is present.

12. The process of claim 7, wherein the surfactant is present.

13. The process of claim 7, wherein the organic carbonate is present in an amount of from about 10 to about 90 percent by weight of the composition.

14. A method of supplying an organic carbonate for use in insecticide compositions, consisting essentially of: providing the organic carbonate for a permitted use in formulations consisting essentially of an insecticide; an organic carbonate; optionally a co-solvent; and optionally a surfactant; wherein the insecticide is O,O-diethyl-O-(2-isopropyl-4-methyl-6-pyrimidinyl)phosphorothioate, or S-[2-bis(ethoxycarbonyl)ethyl]O,O-dimethylphosphorodithioate; wherein the carbonate is an alkylene carbonate containing from 2 to 10 carbon atoms.

15. The method of claim 16, wherein the carbonate is propylene carbonate or ethylene carbonate or both.

16. The method of claim 14, wherein the carbonate is ethylene carbonate or propylene carbonate.

17. The method of claim 14, wherein the co-solvent is present.

18. The method of claim 14, wherein the surfactant is present.

19. The method of claim 14, wherein the organic carbonate is present in an amount of from about 10 to about 90 percent by weight of the composition.

20. A process useful for applying an insecticide composition, comprising:

mixing water and an insecticide composition to form an emulsion, and applying the emulsion on a surface, wherein the insecticide composition consists essentially of an organic carbonate, O,O-diethyl-O-(2-isopropyl-4-methyl-6-pyrimidinyl)phosphorothioate, S-[1,2-bis(ethoxycarbonyl)ethyl]O,O-dimethylphosphorodithioate, optionally a co-solvent, and optionally a surfactant; wherein the carbonate is an alkylene carbonate containing from 2 to 10 carbon atoms.

21. The process of claim 20, wherein the carbonate is propylene carbonate or ethylene carbonate or both.

22. The process of claim 20, wherein the carbonate is ethylene carbonate or propylene carbonate.

23. The process of claim 20, wherein the co-solvent is present.

24. The process of claim 20, wherein the surfactant is present.

25. The process of claim 20, wherein the organic carbonate is present in an amount of from about 10 to about 90 percent by weight of the composition.

* * * * *